United States Patent [19]

Askea et al.

[11] Patent Number: 5,569,858
[45] Date of Patent: * Oct. 29, 1996

[54] VISCOELASTIC MATERIAL TESTING SYSTEM

[75] Inventors: Donald W. Askea, Akron; Jeffrey W. Johnson, Dalton, both of Ohio

[73] Assignee: The B. F. Goodrich Company, Akron, Ohio

[*] Notice: The term of this patent shall not extend beyond the expiration date of Pat. No. 5,458,002.

[21] Appl. No.: 517,637

[22] Filed: Aug. 22, 1995

Related U.S. Application Data

[63] Continuation-in-part of Ser. No. 243,254, May 16, 1994, Pat. No. 5,458,002.

[51] Int. Cl.⁶ ........................................ G01N 3/00
[52] U.S. Cl. .............................. 73/789; 73/788
[58] Field of Search ........................... 73/788, 789, 795, 73/54.01, 54.02, 54.14

[56] References Cited

U.S. PATENT DOCUMENTS

| | | | |
|---|---|---|---|
| 2,886,967 | 5/1959 | Conti | 73/836 |
| 3,379,054 | 4/1968 | Folweiler | 73/789 |
| 3,699,808 | 10/1972 | Ford et al. | 73/789 |
| 3,969,930 | 7/1976 | Prevorsek et al. | 73/789 |
| 4,998,825 | 3/1991 | Hublikar et al. | 73/826 |
| 5,079,956 | 1/1992 | Burhin et al. | 73/846 |
| 5,269,190 | 12/1993 | Kramer | 73/822 |
| 5,458,002 | 10/1995 | Askea et al. | 73/789 |

FOREIGN PATENT DOCUMENTS

| | | | |
|---|---|---|---|
| 0643623 | 3/1937 | Germany | 73/836 |
| 0781672 | 11/1980 | U.S.S.R. | 73/826 |
| 0021049 | of 1912 | United Kingdom | 73/836 |

*Primary Examiner*—Richard Chilcot
*Assistant Examiner*—Max Noori
*Attorney, Agent, or Firm*—Renner, Otto, Boisselle & Sklar; Nestor W. Shust

[57] ABSTRACT

A system for performing a flexometer test includes a balanced beam supporting an anvil upon which a viscoelastic material is placed, the balanced beam being balanced upon a rotatable shaft and pivotable about the axis of the rotatable shaft, an assembly for applying a static load to the material, a hammer opposite the anvil for applying a dynamic strain to the material, and a sensor which senses permanent dimensional changes in the material.

17 Claims, 5 Drawing Sheets

VISCOELASTIC MATERIAL TESTING SYSTEM

RELATED APPLICATIONS

This application is a continuation-in-part of U.S. patent application Ser. No. 08/243,254, filed May 16, 1994 now U.S. Pat. No. 458,002 entitled "Viscoelastic Material Test System" the disclosure of which is incorporated herein by this reference.

FIELD OF THE INVENTION

The invention relates generally to system and method for testing viscoelastic properties of a material, and, more particularly, to a system and method capable of performing flexometer tests on a material to determine temperature rise and permanent set and tests to determine certain fundamental viscoelastic properties of the material, such as the storage modulus and loss modulus.

BACKGROUND OF THE INVENTION

It is often desirable to characterize many of the properties of a specimen or compound to assist in predicting the response of the compound in various applications, to aid in research and development of compounds and as an aid in quality control of a manufactured compound. For example, it is desirable to be able to predict the rolling resistance that a vehicle tire made of a certain rubber compound would have without actually building and testing a tire made of that compound. This rolling resistance can be predicted or inferred from certain characteristics of a rubber sample, such as the temperature change and permanent set of a material when subjected to a flexometer test.

One type of flexometer, the Goodrich type flexometer, is described in Method A of ASTM Designation: D 623, entitled, "Standard Test Methods For Rubber Property—Heat Generation and Flexing Fatigue in Compression." Such a flexometer is relatively inexpensive and small, but provides only limited information on material characteristics, such as temperature change and permanent set. Other devices are available which are able to determine the fundamental viscoelastic properties of a specimen, but are often extremely expensive, large and complicated. Further, many of these machines do not perform flexometer type testing.

It would be desirable to provide a system for performing flexometer tests as well as other tests to determine the fundamental viscoelastic properties of a material which was relatively inexpensive, small and simple to operate.

SUMMARY OF THE INVENTION

The present invention provides a system and method for performing flexometer tests as well as other tests for determining viscoelastic properties of a material. The device is easily converted from a configuration for performing flexometer tests to one for performing tests for fundamental viscoelastic properties by locking a balanced beam member into place and informing a processor of the test to be performed.

In accordance with one aspect of the invention, a device for testing various properties of a viscoelastic material includes a balanced beam supporting an anvil upon which the material is placed, the balanced beam having a fixed state and a movable state, a load assembly for applying a static load to the material when said balanced beam is in a movable state and inducing an initial static strain on said material when said balanced beam is in a fixed state, a hammer opposite the anvil for applying a dynamic strain to the material, a first sensor which senses the dynamic strain applied to the material by the hammer when the balanced beam is in the fixed state, a load cell which detects the force response of the material to the initial static strain load and the dynamic strain when the balanced beam is in the fixed state, and a second sensor which senses permanent dimensional changes in the material when the balanced beam is in the movable state.

In accordance with another aspect of the invention, a device for testing various properties of a viscoelastic material includes a balanced beam supporting an anvil upon which the material is placed, the balanced beam having a fixed state and a movable state, a load assembly for applying a static load to the material when said balanced beam is in a movable state and inducing an initial static strain on said material when said balanced beam is in a fixed state, a hammer opposite the anvil for applying a dynamic strain to the material, a first sensor which senses the dynamic strain applied to the material by the hammer when the balanced beam is in a fixed state, a load cell which detects the force response of the material to the initial static strain and the dynamic strain when the balanced beam is in a fixed state, and a thermocouple which senses the temperature of the material when the balanced beam is in the movable state.

In accordance with another aspect of the invention a method for testing various properties of a viscoelastic material includes the steps of selecting between a first test and a second test to be performed, applying a static load to the material when said second test is selected and inducing an initial static strain on said material when said first test is selected, applying a dynamic strain to the material, sensing the dynamic strain applied to the material when the first test is selected, detecting the force response of the material to the initial static strain and the dynamic strain when the first test is selected, and sensing permanent dimensional changes in the material when the second test is selected.

In accordance with still another aspect of the invention a method for testing various properties of a viscoelastic material includes the steps of selecting between a first test and a second test to be performed, applying a static load to the material when said second test is selected and inducing an initial static strain on said material when said first test is selected, applying a dynamic strain to the material, sensing the dynamic strain applied to the material when the first test is selected, detecting the force response of the material to the initial static strain load and the dynamic strain when the first test is selected, and sensing the temperature of the material when the second test is selected.

In accordance with a further aspect of the invention a system for performing a flexometer test includes a balanced beam supporting an anvil upon which a viscoelastic material is placed, the balanced beam being balanced upon a rotatable shaft and pivotable about the axis of the rotatable shaft, an assembly for applying a static load to the material, a hammer opposite the anvil for applying a dynamic strain to the material, and a sensor which senses permanent dimensional changes in the material.

According to a further aspect of the invention, a system for performing a viscoelastic test includes a balanced beam supporting an anvil upon which a viscoelastic material is placed, the balanced beam being balanced upon a rotatable shaft and selectively pivotable about the axis of the rotatable shaft, a locking assembly including a first contact for contacting the bottom of said balance beam and a second contact for contacting the top of said balance beam, the locking assembly having a first state wherein the beam is free to pivot and a second state wherein the contacts coact to lock the balance beam in a fixed position, an assembly for applying a static force to the material, a hammer opposite the anvil for applying a dynamic strain to the material, at least one sensor for sensing the response of the material to the test, and a controller for controlling the state of the locking assembly.

According to an even further aspect of the invention, an assembly for conversion of a flexometer having a knife-edge fulcrum includes a rotatable shaft rotatably secured in a mounting apparatus, the mounting apparatus being mounted to the frame of the flexometer in replacement of the knife-edge fulcrum, and a replacement pivot block adapted for replacement of a pivot block in the balanced beam of a flexometer, the replacement pivot block further adapted for receipt of at least a portion of the shaft wherein the pivot axis of the shaft and balance beam are coaxial with the point of the knife-edge fulcrum prior to replacement.

The foregoing and other features of the invention are hereinafter fully described and particularly pointed out in the claims, the following description and the annexed drawings setting forth in detail certain illustrative embodiments of the invention, these being indicative, however, of but a few of the various ways in which the principles of the invention may be employed. It will be appreciated that the scope of the invention is to be determined by the claims and the equivalents thereof.

DETAILED DESCRIPTION OF THE INVENTION

Figure 1:
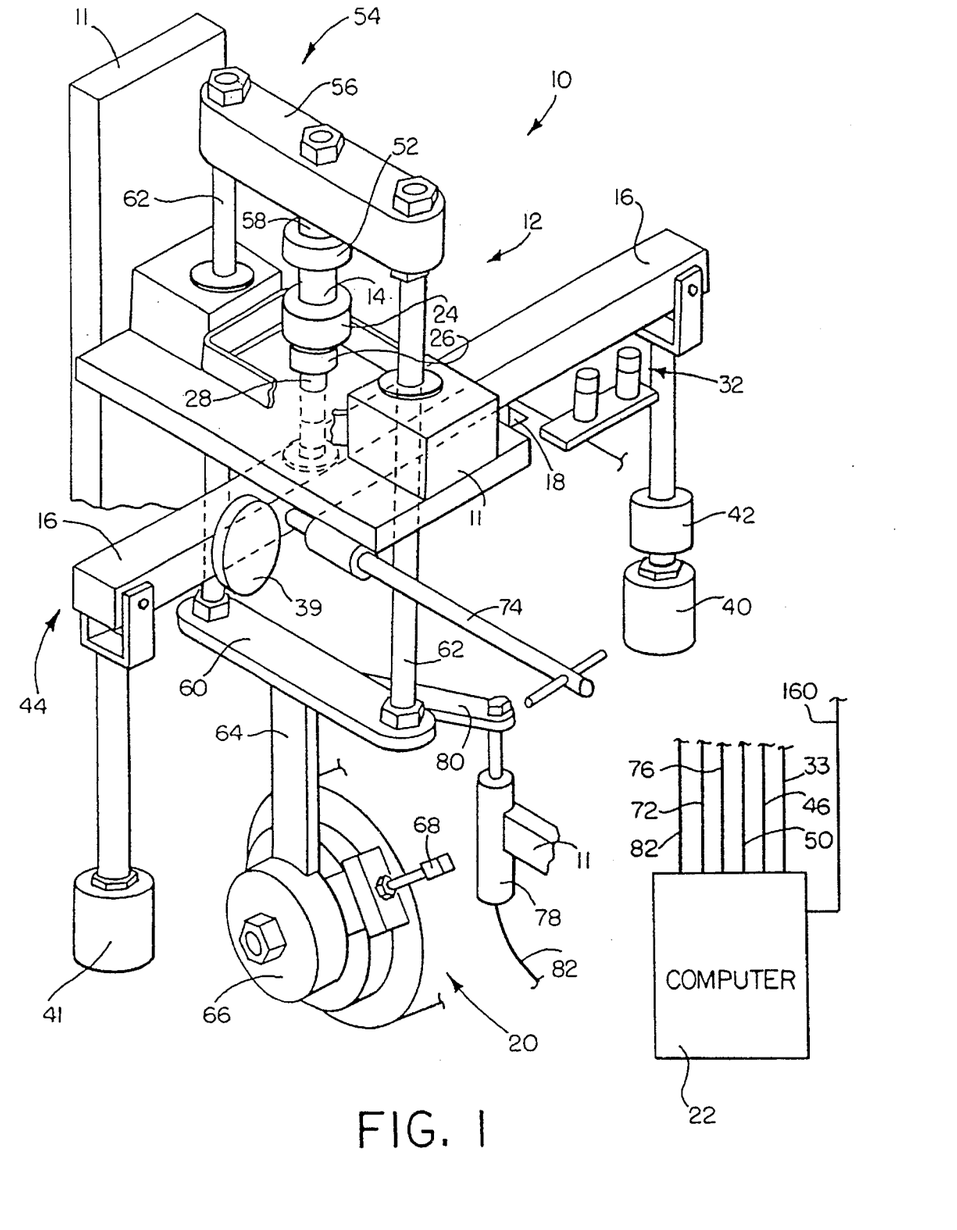
FIG. 1 is a partial isometric view of a test system in accordance with the present invention.

With reference to the drawings and initially to FIG. 1, there is shown a test system 10 in accordance with one embodiment of the present invention. The test system 10 preferably is operable in at least two modes, such as in a mode to perform a flexometer test and a mode to perform a test to determine certain fundamental viscoelastic properties of the test material, for example, the storage modulus, loss modulus and tan delta.

The test system 10 includes a frame 11, a test fixture 12 into which the test specimen 14 is placed, an oven (not shown) surrounding the test specimen and a portion of the test fixture, a high inertia balanced beam 16 balanced on the fulcrum 18, a drive system 20 and a computer 22. The computer 22 controls various aspects of the test, collects test data and computes desired properties of the test specimen 14 from the collected test data in accordance with the test which has been selected for operation. The computer may be any of a number of processing units and related components capable of interacting with remote devices, capable of obtaining and digitizing data and capable of performing the required computation of the data described below.

Figure 2:
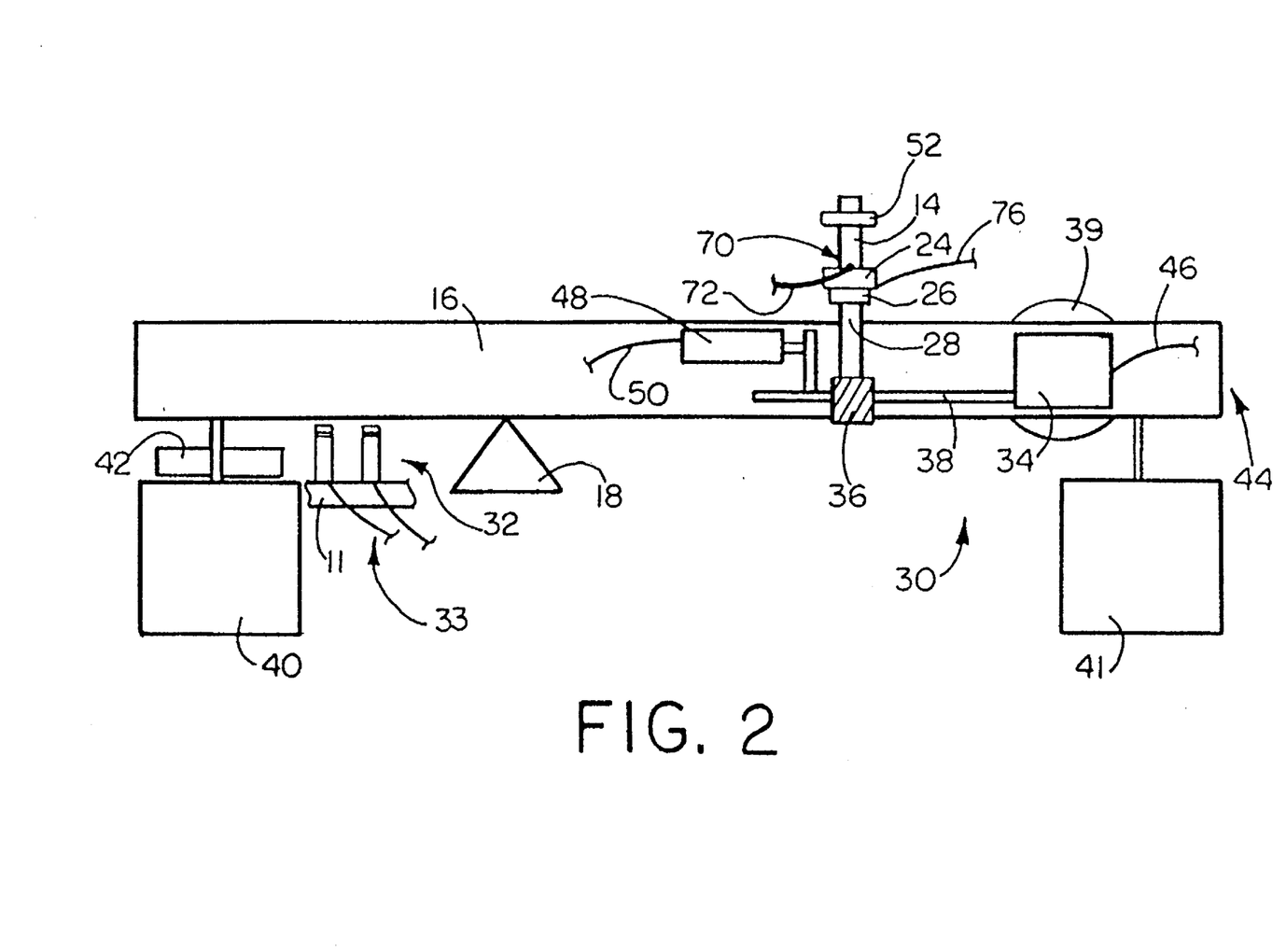
FIG. 2 is a partial side view of the test system of FIG. 1.

The lower portion of the test fixture 12 includes an anvil 24, upon which the test specimen 14 sits, connected to the balanced beam 16 through load cell 26, positional shaft 28, and leveling system 30 shown in FIG. 2. The leveling system 30 includes a pair of magnetic proximity sensors 32 connected to the computer 22 via lines 33 which in combination allow the computer to determine if the balanced beam 16 is level, a levelling motor 34, a drive gear 36 enmeshed with suitable gears on the positional shaft 28, and a drive shaft 38 connecting the levelling motor and drive gear. Rotation of drive shaft 38 by the leveling motor 34 thus causes the drive gear 36 to rotate. The rotation of the drive gear 36 is translated into vertical movement of the positional shaft 28 and anvil 24 through cooperation of the gears of the drive gear and the gears on the positional shaft. A manual leveling crank 39 is also provided which interfaces with the drive shaft 38 to raise or lower the anvil 24 in the same manner as is accomplished by the leveling motor 34.

At either end of the balanced beam 16 is suspended an inertial weight 40, 41 which in combination add inertia to the balanced beam so that it is not substantially effected by the relatively high frequency waveform felt by the anvil 24 during a flexometer test. A load weight 42 may be placed above the rear inertial weight 40 thereby causing a static force to be translated through the balanced beam 16, the positional shaft 28, load cell 26 and anvil 24 to act upon the test specimen 14. Preferably the connections between the rods suspending the weights and the balanced beam 16 are designed to reduce movement of the weights during a test.

When the test system 10 is performing a flexometer test, as described in more detail below, most test specimens 14 will likely undergo a small permanent reduction in their height during the test. This phenomenon is known as "permanent set." A change in the permanent set of the test specimen 14 will cause the forward end 44 of the balanced beam 16 to tend to tip slightly toward the test specimen 14 by virtue of the static loading applied by the load weight 42. Any tipping of the balanced beam 16 is detected by the proximity sensors 32 and reported to the computer 22 which will command the leveling motor 34 via line 46 to rotate in the appropriate direction to raise or lower the positional shaft 28 and anvil 24 relative to the balanced beam. Since the anvil 24 is prevented from moving by the test specimen 14, the balanced beam 16 will adjust its position and thus be maintained level during a flexometer test.

A displacement transducer 48, such as a linear variable differential transformer (LVDT) senses any positional change in the positional shaft 28 and anvil 24 relative to the balanced beam 16. Any such positional changes sensed by the displacement transducer 48 are collected by the computer 22 via a connection 50 between the displacement transducer and the computer and are stored by the computer as changes in the permanent set of the test specimen 14. A displacement transducer, such as an LVDT, may also be used in place of the pair of magnetic proximity sensors 32.

The upper portion of the test fixture 12 includes a hammer 52, as is seen in FIG. 1, positioned above the anvil 24 and abutting the top of the test specimen 14, and a drive frame 54. The drive frame 54 includes an upper cross member 56 connected to the hammer 52 by rod 58, a lower cross member 60, and a pair of vertical posts 62 extending between upper and lower cross members. The posts 62 are vertically, slidably mounted to the frame 11, thus restricting the hammer 52 to vertical movement with the drive frame 54.

The lower cross member 60 of the drive frame 54 is connected to a tie rod 64 eccentrically mounted to the drive system 20 through adjustable disk 66. Rotation of drive system 20 thus causes a vertical cyclic stroke of the tie rod 64, drive frame 54 and hammer 52, the amplitude of which is determined by the degree of eccentricity of the connection between the tie rod and drive system. The degree of eccentricity and thus the amplitude of the stroke of the hammer 52 is adjustable through the adjustment bolt 68.

To perform a flexometer test with the test system 10, an operator will place a test specimen 14 of the viscoelastic material to be tested between the anvil 24 and hammer 52. The operator then adds the appropriate load weight 42 to the rear inertial weight 40, levels the balanced beam 16 using the leveling crank 39, sets the desired stroke of the hammer 52 through the adjustment bolt 68, and informs the computer 22 that a flexometer test is to be performed. Some test variables, such as the oven temperature, the frequency of the hammer stroke, and the test duration, may be set by entering the variables into the computer 22 or by adjusting them manually when the computer is not set up to control the test variable. When the test is commenced, the hammer 52 will cycle vertically thereby exerting a dynamic strain on the test sample 14 while the sample is concurrently subjected to a static load from the load weight 42. A thermocouple 70 (See FIG. 2), preferably mounted to the top of the anvil 24 and positioned below the test sample 14 senses the temperature of the test sample throughout the test and transfers the sensed temperature as an electrical signal to the computer 22 over the line 72 for storage as a function of time. Any adjustments made to level the balanced beam 16 during the test in response to changes in permanent set of the test sample 14 are sensed by the displacement transducer 48 and transferred to the computer 22 over the line 50.

Figure 3:
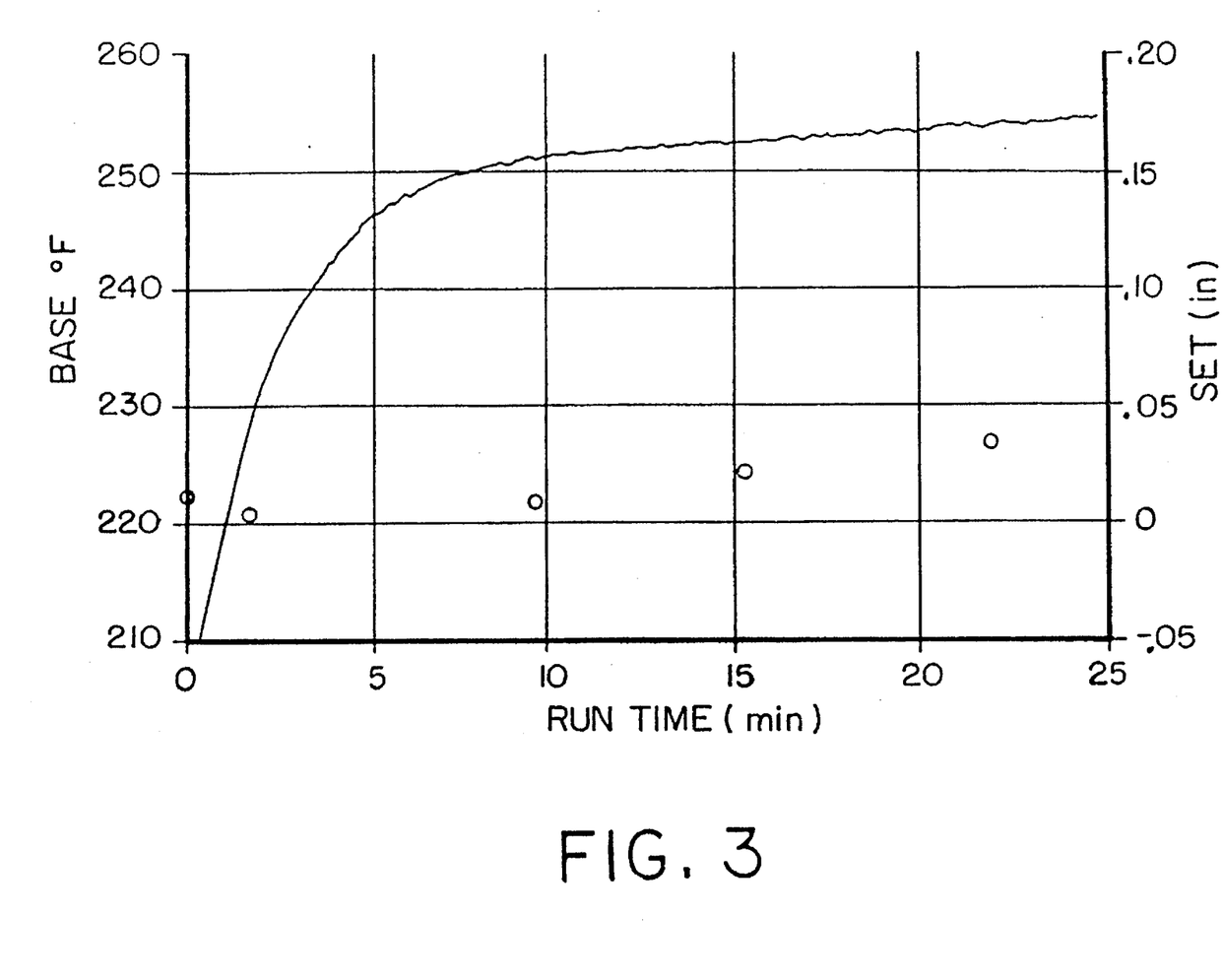
FIG. 3 is a graphical plot of temperature as a function of run time in minutes for a flexometer test.

Once the flexometer test is completed, typically after around 25 minutes, the operator can command the computer to print the results or to display or print a graphical plot of the desired test results, such as a plot of temperature and permanent set for the test sample 14 as a function of time as shown in FIG. 3.

When it is desired to perform a different test, such as a dynamic mechanical test to determine certain fundamental viscoelastic properties of a test specimen, the test system 10 is readily reconfigured to change testing capabilities. To perform a dynamic mechanical test (DMT), the operator slides pin 74, shown in FIG. 1, to engage the balanced beam 16. As the pin 74 is slidably mounted to the frame 11, the balanced beam is then supported at two points, the fulcrum 18 and the pin 74 and thus is fixed during the test. Since the balanced beam 16 is fixed, any desired initial static strain can be induced on the specimen 14 by rotating the leveling crank 39 (FIG. 2).

The operator then sets the desired stroke of the hammer 52 through the adjustment bolt 68, and informs the computer 22 that a dynamic mechanical test is to be performed. Some test variables, such as the oven temperature, the frequency of the hammer stroke, and the test duration, may be set by entering the variables into the computer 22 or by adjusting them manually when the computer is not set up to control the test variable.

Figure 4:
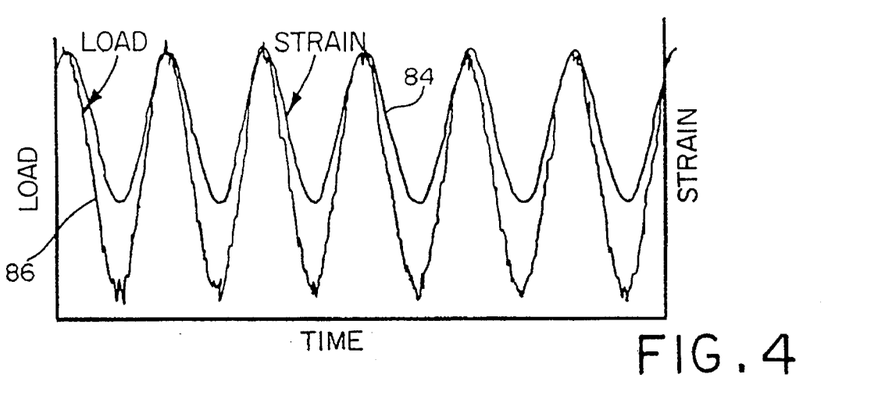
FIG. 4 is a superimposed plot of strain applied to a test specimen and the waveform of the force response of the specimen to the applied strain as a function of time.

When the test is commenced, the hammer 52 will cycle vertically thereby exerting a dynamic strain on the test sample 14 while the sample is concurrently subjected to a static load by the adjustment to the height of the anvil 24. During the test the computer 22 will sample the signal output by the load cell 26 over line 76 to develop a waveform of the force response of the test material 14 to the applied dynamic strain over time. As the drive system 20 rotates and drives the drive frame 54 and hammer 52 through their stroke, the position of the drive frame, and thus the position of the hammer, is sensed by the positional transducer 78 (See FIG. 1) connected between the frame 11 and an extension arm 80 of the drive frame 54. The positional transducer 78 may be a linear variable differential transformer or a similar device which develops an electrical signal as a function of linear position and transfers the signal to the computer 22 over line 82. During the test the output of the positional transducer 78 over the line 82 is sampled by the computer 22, which develops a waveform of the dynamic strain applied to the test specimen by correlating the sampled data with time. FIG. 4 illustrates the waveform 84 of the applied strain exerted by the hammer 52 on the test sample 14 and the force response waveform 86 of the test sample for an exemplary test.

At the conclusion of the test the computer 22 will calculate the phase shift or difference between the two waveforms using a suitable technique such as a Fast Fourier Transform algorithm. The complex modulus (E*) of the test sample can then be calculated and reduced to the storage modulus (E') and the loss modulus (E"), as well as to tan delta (E"/E') for the test sample through known methods.

Figure 5:
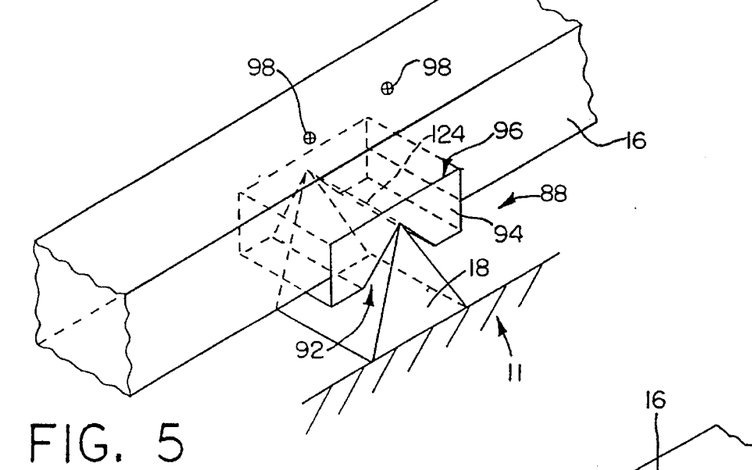
FIG. 5 is an enlarged view of the pivot assembly of a convention flexometer having a knife-edge fulcrum.

The balanced beam 16 of a standard flexometer typically has a pivot assembly 88 wherein the balanced beam 16 is balanced upon a knife-edge fulcrum 18, as shown in FIG. 5. The knife-edge portion of the fulcrum 18 typically has about a 60 degree apex 90 and fits into a generally 90 degree notch 92 provided in a pivot block 94 secured to a recess 96 in the bottom of the balanced beam 16. The pivot block 94 is typically secured to the balanced beam 16 through a number of screws or bolts 98 and is made of a material resistant to scratching or abrasion from the knife-edge. While the knife-edge fulcrum 18 and notch 92 provide, at least initially, a relatively low friction and precise pivot axis for the balanced beam 16, the knife-edge may wear or chip over time, especially during certain high stress tests, such as a blow out test where a specimen is tested under a large dynamic load until it fails.

Figure 6:
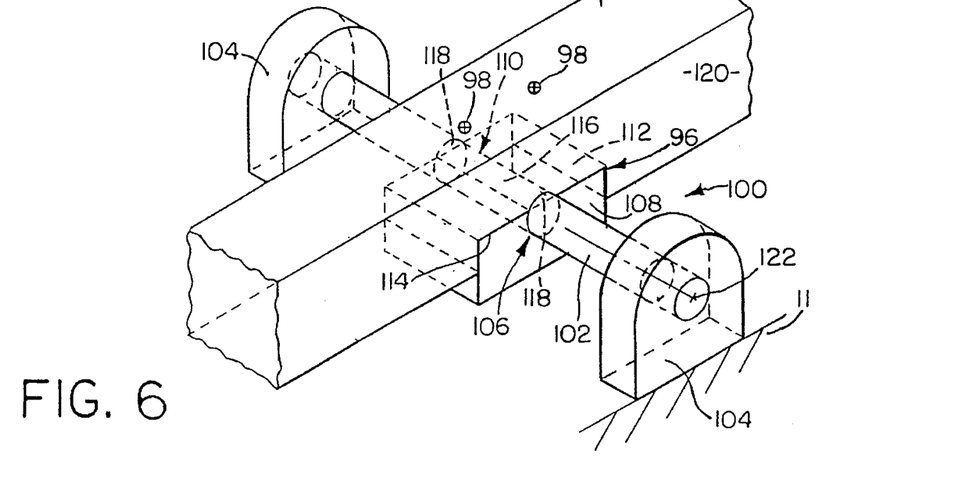
FIG. 6 is an enlarged view of an alternate pivot assembly.

An alternate embodiment of the pivot assembly 100 is shown in FIG. 6. The pivot assembly 100 includes a shaft 102 rotatably secured at either side of the beam 16 by pillow blocks 104. The pillow blocks 104 are in turn mounted to the frame 11 of the test system 10. The pillow blocks 104 may be conventional ball bearing assemblies with the seals, shields and viscous grease preferably removed to reduce the friction of the shaft rotating within the pillow block. The shaft 102 passes through an accommodating passage 106 in a pivot block 108 sized to fit within the recess 96 in the bottom of the balanced beam 16 and attached to the balanced beam, such as by the mounting screws 98. Preferably, the passage 106 extending through the pivot block 108 is generally in the form a truncated cylinder offset toward the balanced beam 16 to form a rectangular opening 110 in the face 112 of the pivot block confronting the face 114 of the recess 96 in the balanced beam. The shaft 102 then preferably has a flat surface 116 formed in the top surface thereof of the approximate size of the rectangular opening 110 centrally located between the pillow blocks 104. The flat surface 116 of the shaft 102 thus confronts and contacts the face 114 of the recess 96 preventing rotation of the shaft relative to the balanced beam 16 and thus confining the balanced beam to pivot about the central axis of the shaft. As the flat surface 116 of the shaft 102 has a length approximately equal to the width of the balanced beam 16, the faces 118 of the shaft extending perpendicular to the flat surface 116, corresponding to the full diameter of the shaft, confront the sides 120 of the balanced beam and prevent relative axial movement between the balanced beam and the shaft.

Through the use of the pivot assembly 100, the balanced beam 16 pivots relatively freely but is secured relative to the frame 11 thus preventing the balanced beam 16 from bouncing on the pivot axis even under extreme test conditions. This reduces wear on the pivot assembly 100 and promotes more accurate testing over a longer life.

The pivot assembly 100 can also be used as a replacement kit to modify many existing flexometers which include a knife-edge pivot assembly 88 as shown in FIG. 5. In such a case the pivot block 108 (FIG. 6) is sized to fit into the existing recess 96 in the balanced beam 16 and is adapted to mount to the balanced beam in the same way as the pivot block 94 was mounted, such as through the screws 98. Preferably, the axis of rotation 122 of the shaft 102 is positioned at the pivot axis 124 of the knife-edge fulcrum 18 and thus the balanced beam maintains the same pivot point after the pivot assembly 88 is replaced with pivot assembly 100. As the pivot block 108 and shaft 102 are positioned at the pivot point of the pivot assembly 100, the added components do not effectively add inertial weight to balanced beam or appreciable effect the performance of flexometer. To replace an existing pivot assembly 88 with the pivot assembly 100, the knife-edge fulcrum 18 and pivot block 94 of the pivot assembly 88 are removed and are replaced with pillow blocks 104, pivot block 108 and shaft 102. Preferably no other modifications to the flexometer are necessary.

Figure 7:
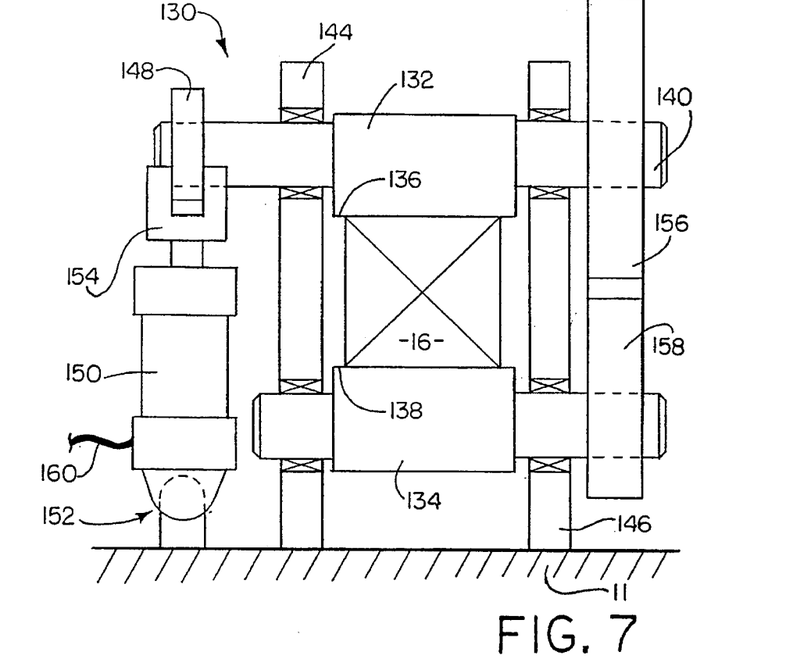
FIG. 7 is a view of an automatic locking assembly looking down the balanced beam.
Figures 8, 9:
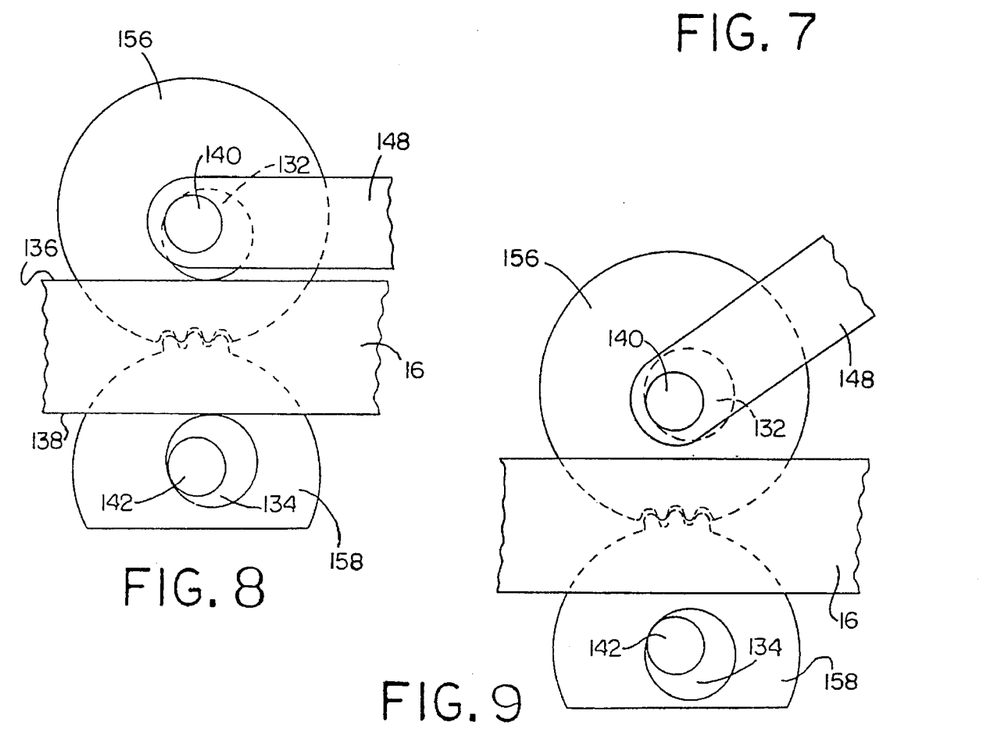
FIG. 8 is a partial side view of the automatic locking assembly of FIG. 7 with the supporting bearings removed for clarity and the balanced beam in a fixed state.
FIG. 9 is a partial side view of the automatic locking assembly of FIG. 7 with the supporting bearings removed for clarity and the balanced beam in a free state.

Referring to FIGS. 7 through 9, there is shown an automatic locking assembly 130 for locking the balanced beam 16 in place during all or part of a test. The automatic locking assembly 130 performs the same function as the manual locking pin 74 shown in FIG. 1 and is used to lock the balanced beam 16 in place in a level condition during a non-flexometer tests as well as at the beginning and end of a flexometer test. The locking assembly 130 is preferably positioned just aft of the pivot assembly 100 between the pivot assembly and the leveling sensors 32.

The locking assembly 130 includes an upper and a lower eccentric cam 132 and 134, respectively, with the upper cam 132 being positioned above the balanced beam 16 for selective contact with the top surface 136 of the beam and the lower cam 134 being positioned below balanced beam for selective contact with the bottom surface 138 of the beam. The cams 132 and 134 are rotatable between at least two positions and coact with the pivot assembly 100 to lock the balanced beam 16 into a level position when in one rotational position and to permit the balanced beam to pivot around the pivot axis 122 when in a second rotational position.

Each cam 132, 134 is held in place relative to the balanced beam 16 and rotated through a connection to a shaft 140, 142, respectively, secured within bearing assemblies 144 and 146 disposed on either side of the balanced beam.

Rotational movement of the upper shaft 140, to which the upper cam 132 is secured, is accomplished through a lever arm 148 and an actuator 150. The actuator 150 may be one of several known types, including a hydraulic or pneumatic cylinder, and is secured to the frame 11 through a suitable connection 152 permitting angular movement of the actuator relative to the frame. The rod 154 of the actuator is rotatably linked to the lever arm 148 which is fixed to and extends radially away from the upper shaft 140. The lever arm 148 thus translates linear movement of the rod 154 into rotational movement of the upper shaft 140 and upper cam 132.

Located on the upper shaft 140 distal from the lever arm 148 is an upper gear 156 which rotates with the upper shaft. The upper gear 156 is enmeshed with a like lower gear 158 affixed to the lower shaft 142. Consequently, rotation of the upper shaft 140 and upper gear 132 by the actuator 150 is communicated to the lower shaft 142 and lower gear 134 so that the cams turn together. The degree of eccentricity of the cams is such that a small travel of the actuator rod 154 causes the cams to selectively engage the balanced beam 16 and secure it in a locked, level position or to retract sufficiently from the balanced beam that the beam can pivot unhindered to the extent necessary to perform a flexometer test.

The actuator 150 and thus the position of the cams 132, 134 is preferably controlled by a processor, such as the computer 22, over line 160 in accordance with the specific test being performed. For example, before the initiation of a flexometer test the computer 22 would control the actuator 150 to fully retract the actuator rod 154 thus causing the upper and lower cams 132 and 134 to rotate to a position contacting the top and bottom surfaces 136 and 138, respectively, of balanced beam 16 and locking the beam in a level condition, as shown in FIGS. 7 and 8. After the test has begun and the response of the machine to the varying stresses has settled, the computer 22 will then cause the actuator 150 to extend the actuator rod 154 and the cams to rotate away from the balanced beam 16 to allow it to pivot in a free condition during the remainder of the test, as shown in FIG. 9. At the timed completion of the flexometer test or upon the detection by the computer of another condition such as when the response of the material to the test has changed suddenly, the computer 22 will cause the actuator 150 to retract the actuator rod 154 thereby rotating the cams 132 and 134 into contact with the balanced beam 16 to lock it in a fixed state. The test can then stopped without significant risk of damage to the balanced beam 16 or pivot assembly 100 as the system slows to a stop. The automatic locking assembly 130 thus allows a test, such as a flexometer test, to be performed unattended.

When the operator instructs the test system 10 to perform a test requiring a fixed beam, such as a test of certain fundamental viscoelastic properties, the computer 22 will control the actuator 150 to fully retract the actuator rod 154 thus causing the upper and lower cams 132 and 134 to rotate to a position contacting the top and bottom surfaces 136 and 138, respectively, of balanced beam 16 and locking the beam in a fixed, level condition throughout the test.

What is claimed is:

1. A system for performing a flexometer test, comprising:
   a balanced beam supporting an anvil upon which a viscoelastic material is placed, the balanced beam being balanced upon a rotatable shaft and pivotable about the axis of the rotatable shaft;

an assembly for applying a static load to the material;

a hammer opposite the anvil for applying a dynamic strain to the material; and a sensor which senses permanent dimensional changes in the material.

2. The system of claim 1, wherein the shaft is rotatably secured within a pair of support bearings.

3. The system of claim 1, wherein the shaft includes a flat area in contact with the bottom of the balanced beam.

4. The system of claim 3, wherein the shaft is secured to the balanced beam through a pivot block.

5. The system of claim 1, further including a locking assembly including a first contact for contacting the bottom of the balance beam and a second contact for contacting the top of the balance beam, the locking assembly having a first state wherein the beam is free to pivot and a second state wherein the contacts coact to lock the balance beam in a fixed position.

6. A system for performing a viscoelastic test, comprising:
 a balanced beam supporting an anvil upon which a viscoelastic material is placed, the balanced beam being balanced upon a rotatable shaft and selectively pivotable about the axis of the rotatable shaft;
 a locking assembly including a first contact for contacting the bottom of said balance beam and a second contact for contacting the top of said balance beam, the locking assembly having a first state wherein the beam is free to pivot and a second state wherein the contacts coact to lock the balance beam in a fixed position;
 an assembly for applying a static force to the material;
 a hammer opposite the anvil for applying a dynamic strain to the material;
 at least one sensor for sensing the response of the material to the test; and
 a controller for controlling the state of the locking assembly.

7. The system of claim 6, wherein the controller controls the locking assembly to be in the second state at the beginning and at the end of a flexometer test.

8. The system of claim 6, wherein the controller controls the locking assembly to be in the first state during an intermediate portion of a flexometer test.

9. The system of claim 6, wherein the controller controls the locking assembly to be in the second state throughout a test.

10. The system of claim 6, wherein the contacts are eccentric cams.

11. The system of claim 10, wherein the cams are affixed to rotatable shafts.

12. The system of claim 11, wherein the rotatable shafts are rotated by an actuator and lever arm linkage.

13. The system of claim 11, wherein a gear is secured to each rotatable shaft, the gears being enmeshed to communicate rotation from one shaft to the other shaft.

14. The system of claim 11, wherein the shafts are rotatably secured within a pair of support bearings.

15. An assembly for conversion of a flexometer having a knife-edge fulcrum supporting a balanced beam, comprising:
 a rotatable shaft rotatably secured in a mounting apparatus, the mounting apparatus being mounted to the frame of the flexometer in replacement of the knife-edge fulcrum; and
 a replacement pivot block adapted for replacement of a pivot block in the balanced beam of a flexometer, the replacement pivot block further adapted for receipt of at least a portion of the shaft wherein the pivot axis of the shaft and balanced beam are coaxial with the point of the knife-edge fulcrum prior to replacement.

16. The assembly of claim 15, wherein the shaft includes a flat area in contact with the bottom of the balanced beam.

17. The system of claim 15, wherein the mounting apparatus includes a pillow block on each side of the balanced beam.

* * * * *